United States Patent
Ueda

[11] Patent Number: 5,885,993
[45] Date of Patent: Mar. 23, 1999

[54] REMEDY FOR PANCREATITIS

[75] Inventor: Fusao Ueda, Shiga, Japan

[73] Assignee: Nippon Shinyaku Company, Limited, Kyoto, Japan

[21] Appl. No.: 913,165
[22] PCT Filed: Mar. 8, 1996
[86] PCT No.: PCT/JP96/00581
  § 371 Date: Sep. 9, 1997
  § 102(e) Date: Sep. 9, 1997
[87] PCT Pub. No.: WO96/28164
  PCT Pub. Date: Sep. 19, 1996

[30] Foreign Application Priority Data

Mar. 9, 1995 [JP] Japan ................................. 7-049411

[51] Int. Cl.$^6$ ................................................. A61K 31/53
[52] U.S. Cl. ............................................ 514/245; 544/204
[58] Field of Search .............................. 514/245; 544/209

[56] References Cited

FOREIGN PATENT DOCUMENTS

| | | |
|---|---|---|
| 57-35587 | 2/1982 | Japan . |
| 58-55423 | 4/1983 | Japan . |
| 59-104320 | 6/1984 | Japan . |
| 2-510927 | 7/1991 | Japan . |
| 3-503459 | 2/1992 | Japan . |
| 4-295427 | 10/1992 | Japan . |
| 4-501474 | 1/1993 | Japan . |
| WO96/04914 | 2/1996 | WIPO . |

OTHER PUBLICATIONS

Chemical Abstracts 106:95920u.
Japanese Journal of Gastroenterology vol. 91—Sep. 1994 2,4–Diamino–6–(2.5–dichlorophenyl)–s–trianzinemaleate, by Ueda et al.

*Primary Examiner*—James H. Reamer
*Attorney, Agent, or Firm*—Graham & James LLP

[57] ABSTRACT

The invention relates to a therapeutic drug for pancreatitis which comprises a compound of the following general formula [I] or a salt thereof, or a solvate thereof.

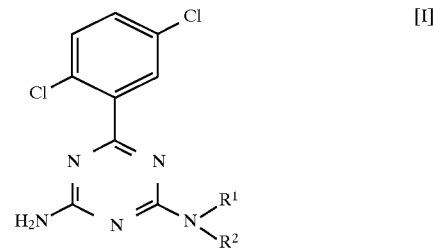

In the above formula, $R^1$ and $R^2$ may be the same or different and each represents hydrogen, alkyl which may be substituted, aralkyl, arylalkenyl, or aryl, or $R^1$ and $R^2$ taken together with the adjacent N atom, i.e. in the form of $NR^1R^2$, represent a 4- through 8-membered cyclic amino group, which cyclic amino group may contain nitrogen, oxygen, or sulfur as a ring member in addition to the above-mentioned N atom and may be further substituted.

9 Claims, No Drawings

REMEDY FOR PANCREATITIS

TECHNICAL FIELD

The present invention relates to a remedy for pancreatitis.

BACKGROUND ART

Pancreatitis is classified mainly into acute pancreatitis caused by autodigestion due to intracellular activation of the digestive enzymes produced in the exocrine pancreas and chronic pancreatitis which, by fibrosis, progresses to irreversible functional failure of the pancreas. The etiology of pancreatitis remains to be fully elucidated as yet. The therapeutic approach to acute pancreatitis consists of, to start with, conservative therapies such as removal of causes, pancreatic protection, arrest of pancreatic autodigestion, and removal of pain. Referring to pharmacotherapy, arrest of pancreatic autodigestion is sought by the administration of proteolytic enzyme inhibitors such as gabexate mesylate, camostat mesylate, nafamostat mesylate, urinastatin, and aprotinin. The treatment of chronic pancreatitis consists of therapies analogous to that of acute pancreatitis in relapsing episodes involving abdominal pain and prohibition of alcohol intake and restriction of fat-rich food in remissions. The protease inhibitors in use today for the pharmacotherapy of pancreatitis are only effective in relieving some of the symptoms of pancreatitis and have various side effects, thus being not clinically satisfactory enough.

Meanwhile, the list of therapeutic drugs for pancreatitis under development today includes several compounds such as loxiglumide, which is a cholecystokinin antagonist, and FK480, which is a protease inhibitor. Furthermore, it has been reported that the antiulcer compound irsogladine maleate [2,4-diamino-6-(2,5-dichlorophenyl)-1,3,5-triazine maleate], which is structurally akin to the compound of the invention, proved efficacious in an animal model of cerulein (hereinafter referred to briefly as Cn)-induced acute pancreatitis (the Proceedings of the 36th Congress of The Japanese Society of Gastroenterology, p.266).

The inventors of the present invention discovered that the 2-amino-4-substituted amino-6-(2,5-dichlorophenyl)-1,3,5-triazine derivative according to the invention has antihepatitis activity, thus being a compound of value as a therapeutic drug for hepatitis, and already filed a patent application (WO96/04914).

DISCLOSURE OF INVENTION

In view of the retarded progress in the development of therapeutic drugs for pancreatitis, the inventors of the present invention endeavored to develop a substance having satisfactory antipancreatitis activity. The object of the invention, therefore, is to provide a therapeutic drug for pancreatitis which is more effective and less liable to elicit adverse drug reactions than the prior art therapeutic drugs for pancreatitis.

The inventors discovered that the compound of the following general formula [I] suppresses the onset of pancreatitis as such in mammals and has a very low toxic potential and accordingly have completed the instant invention.

The present invention relates to a therapeutic composition for pancreatitis which comprises a compound of the following general formula [I] or a salt thereof, or a solvate thereof, as an active ingredient.

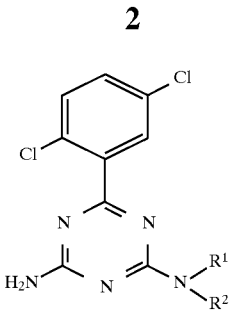

Referring to the above formula, $R^1$ and $R^2$ may be the same or different and each represents hydrogen, alkyl which may be substituted, aralkyl, arylalkenyl, or aryl or $R^1$ and $R^2$ in combination with the adjacent N atom, i.e. in the form of $NR^1R^2$, represent a 4-through 8-membered cyclic amino group, which cyclic amino group may contain nitrogen, oxygen, or sulfur as a ring member in addition to said N atom and may also be substituted.

The present invention is predicated on the finding that said 2-amino-4-substituted amino-6-(2,5-dichlorophenyl)-1,3,5-triazine known to have antihepatitis activity is possessed of antipancreatitis activity which is quite unrelated with antihepatitis activity.

As will be set forth in the test examples presented hereinafter, the compound of the present invention has by far superior efficacy compared with irsogladine maleate [2,4-diamino-6-(2,5-dichlorophenyl)-1,3,5-triazine maleate] in an animal model of pancreatitis which presents with a histological picture closely simulating the clinical picture of acute pancreatitis. Thus, in the rat model of pancreatitis induced by administration of cerulein (Cn), a pancreatitis-inducing chemical, plus water immersion stress loading (referred to briefly as St), which is hereinafter referred to briefly as Cn+St pancreatitis, the compound of the invention exhibits very potent inhibitory activity as compared with irsogladine maleate which shows only moderate activity.

The present invention is now described in further detail.

The "alkyl" mentioned for $R^1$ and $R^2$ includes straight-chain or branched alkyl groups of 1–10 carbon atoms, such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl, isooctyl, n-nonyl, isononyl, n-decyl, and isodecyl. Preferred are $C_{1-4}$ alkyl groups. Such alkyl groups may each be substituted by one, two or three substituent groups, whether similar or dissimilar, as selected from the group consisting of hydroxy, alkoxy, amino, monoalkylamino, dialkylamino, arylamino, cyclic amino, carboxy, carbamoyl, aryloxy, and acyloxy. The alkyl moiety of such substituent groups may be a straight-chain or branched $C_{1-4}$ alkyl group such as methyl, ethyl, n-propyl, isopropyl, n-butyl, isobutyl, sec-butyl, and tert-butyl. The alkoxy mentioned above includes straight-chain or branched $C_{1-4}$ alkoxy groups such as methoxy, ethoxy, n-propoxy, isopropoxy, n-butoxy, isobutoxy, sec-butoxy, and tert-butoxy. The acyl of said acyloxy includes $C_{1-6}$ alkanoyl (e.g. formyl, acetyl, propionyl, butyryl, valeryl, hexanoyl), $C_{7-10}$ aroyl (e.g. benzoyl), and heterocyclylcarbonyl (e.g. nicotinoyl). Particularly preferred is benzoyl. The cyclic amino mentioned as a substituent for the alkyl includes the species mentioned hereinafter for $NR^1R^2$ but is preferably piperidino, piperazin-1-yl, or morpholino. The cyclic amino group may be substituted by $C_{7-14}$ aralkyl groups to be described hereinafter. The aryl includes those groups which will be described hereinafter.

The "aralkyl" mentioned for $R^1$, $R^2$ includes $C_{7-14}$ aralkyl, such as benzyl, phenethyl, phenylpropyl, phenylbutyl, 1-naphthylmethyl, 2-naphthylmethyl, or diphenylmethyl. Preferred is benzyl.

The "arylalkenyl" mentioned for $R^1$, $R^2$ includes $C_{8-10}$ arylalkenyl such as cinnamyl or 3-phenylallyl, among others.

The "aryl" mentioned for $R^1$, $R^2$ includes $C_{6-13}$ aryl such as phenyl, 1-naphthyl, 2-naphthyl or biphenyl. Preferred is phenyl.

$R^1$ and $R^2$ preferably represent mono-substituted $C_{1-4}$ alkyl, more preferably hydroxy-substituted $C_{1-4}$ alkyl, and most preferably hydroxyethyl.

The "cyclic amino" represented by $NR^1R^2$ includes saturated and unsaturated cyclic amino groups, such as azetidin-1-yl, pyrrolidin-1-yl, 3-pyrrolin-1-yl, piperidino, hexamethyleneimino, octahydroazocin-1-yl, piperazin-1-yl, homopiperazin-1-yl, morpholino, and thiomorpholino. Those cyclic amino groups may respectively have 1–4 substituent groups selected from the group consisting of hydroxy, oxo, carboxy, alkyl, hydroxyalkyl, aryloxyalkyl, aminoalkyl, alkylsulfonylaminoalkyl, alkylsulfonylamino, alkylsulfonylaralkyl, alkylsulfonyl, aryl, aralkyl, and 2-pyrimidinyl. The alkyl moiety of such substituent groups includes straight-chain or branched $C_{1-4}$ alkyl such as methyl, ethyl, n-propyl, isopropyl, n-butyl, isobutyl, sec-butyl, and tert-butyl. The aryl and aralkyl moieties of such substituents include those groups respectively mentioned hereinbefore.

$NR^1R^2$ is preferably a 5- or 6-membered cyclic amino group which is either unsubstituted or substituted by one or two similar or dissimilar substituent groups and more preferably pyrrolidin-1-yl, piperidino, or morpholino. Particularly preferred is pyrrolidin-1-yl or morpholino. The preferred substituent for said cyclic amino is hydroxy or hydroxyalkyl. The hydroxyalkyl mentioned just above is preferably hydroxymethyl.

When the alkyl mentioned for $R^1$, $R^2$ or the represented by $NR^1R^2$ is substituted by an aryl or aryl-containing group, the aryl moiety may have 1–3 substituent groups, whether similar or dissimilar, as selected from the group consisting of said $C_{1-4}$ alkyl or alkoxy groups.

The compound [I] of the invention may be used in the free form or in the form of a pharmacologically acceptable acid addition salt, such as salts with inorganic acids (e.g. hydrochloride, sulfate, nitrate, phosphate, hydrofluoride, hydrobromide) or salts with organic acids (e.g. acetate, tartrate, lactate, citrate, fumarate, maleate, succinate, methane-sulfonate, ethanesulfonate, benzenesulfonate, toluene-sulfonate, naphthalenesulfonate, camphorsulfonate). The compound (I) can also be used in the form of a solvate.

The solvate of the compound of the invention includes the hydrate, ethanolate, and other pharmacologically acceptable solvates.

The compound [I] of the invention can be prepared, for example by the following process [WO96/04914].

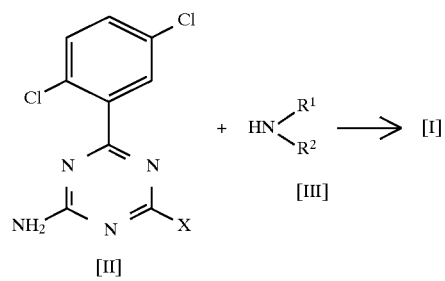

In the above reaction scheme, $R^1$ and $R^2$ are as defined hereinbefore; X represents halogen such as chlorine or bromine.

Thus, [I] can be prepared by reacting halotriazine derivative [II] with amine [III] in the presence of a base in an inert solvent at 0°–200° C., preferably 25°–100° C. The reaction solvent that can be used includes aprotic polar solvents such as acetonitrile, dimethyl sulfoxide and N,N-dimethylformamide (DMF); ethers such as tetrahydrofuran, dimethoxyethane, diethyl ether and dioxane; glymes such as methylcellosolve and ethylene glycol dimethyl ether; halogenated hydrocarbons such as methylene chloride and chloroform; hydrocarbons such as benzene, toluene and xylene; and mixtures of those solvents. The base that can be used includes inorganic bases such as alkali metal carbonates (e.g. potassium carbonate, sodium carbonate), alkali metal hydrogen carbonates (e.g. potassium hydrogen carbonate, sodium hydrogen carbonate) and alkali metal hydroxides (e.g. potassium hydroxide, sodium hydroxide) and organic bases such as triethylamine and pyridine. In lieu of such a base, the amine ($HNR^1R^2$) may be used in excess.

The reaction time depends on species of the starting compounds, base, and solvent but may range from several minutes to 24 hours.

The molar ratio of amine [III] to compound [II] is generally at least equimolar and preferably 1–1.2 molar. The amount of the base is generally at least equimolar and preferably 1–2 molar equivalents with respect to [II].

The compound [Ia] of the invention wherein $R^1$ and/or $R^2$ is alkyl substituted by amino or hydroxy in any desired position or the cyclic amino group represented by the formula $NR^1R^2$ is substituted by aminoalkyl, hydroxyalkyl or hydroxy in any desired position or positions can be prepared by -the following alternative process.

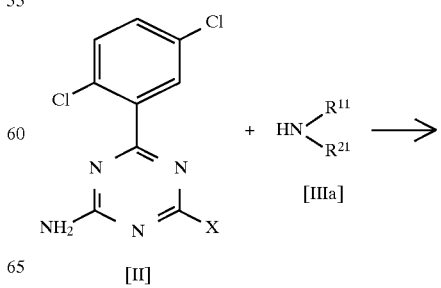

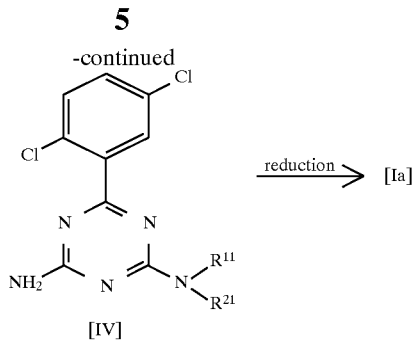

[IV]

In the above reaction schema, X is as defined hereinbefore; $R^{11}$ and $R^{21}$ independently represent alkyl substituted by carbamoyl, cyano, an ester residue, or oxo or $NR^{11}R^{21}$ represent cyclic amino substituted by carbamoyl, cyano, an ester residue, or oxo.

Thus, compound [Ia] can be prepared by reacting the corresponding amine [IIIa] substituted by carbamoyl, cyano, ester residue or oxo with halotriazine derivative [II] under the same conditions above to give compound [IV] and then reducing this compound [IV].

This reduction reaction can be carried out by any of the per se known methods. For example, compound [IV] can be reduced by means of a metal hydrogen complex compound such as lithium aluminum hydride or sodium borohydride. The reduction of [IV] with lithium aluminum hydride, for instance, can be carried out using 0.25–1.0 molar equivalents of $LiAlH_4$ in 2–100 volumes of an ethereal solvent such as diethyl ether, tetrahydrofuran, dimethoxyethane, or dioxane at –50°–30° C. for 0.5–10 hours, to thereby provide the compound [Ia] of the invention. When sodium borohydride is used, the reaction can be carried out in a protoic solvent, e.g. methanol, ethanol, or isopropyl alcohol, in lieu of said ethereal solvent in otherwise the same manner as above.

The starting compound [II] can be prepared by the known production technology (JP Kokai S51-70781). Compounds [III] and [IIIa] can be purchased from commercial sources or synthesized by a conventional manner starting with commercial compounds.

Some species of the compound of the invention have a asymmetric carbon(s) and may therefore be optically active but such optical isomers and mixtures thereof also fall within the scope of the invention.

Such optically active compounds can be isolated by means of a chiral column or by an optical resolution method utilizing their basicity which comprises using an optically active acid (tartaric acid, dibenzoyltartaric acid, mandelic acid, 10-camphorsulfonic acid, etc.). They can also be synthesized starting with optically active compounds [III] or [IIIa] prepared in advance.

The compound [I] of the invention can be caused to form salts in the per se known manner. For example, the hydrochloride of compound [I] according to the invention can be provided by dissolving [I] in an alcoholic solution of hydrogen chloride.

Among species of compound [I] of the invention, the carboxy-containing compounds can be changed to salts in the per se known manner. The salts may for example be alkali metal salts such as the corresponding sodium salts and potassium salts, and alkaline earth metal salts such as the corresponding calcium salts. For example, the alkali metal salt of compound [I] according to the invention can be obtained by adding preferably one equivalent of sodium hydroxide, potassium hydroxide or the like to carboxy-containing compound [I] in an alcoholic solvent. The alkaline earth metal salt of compound [I] according to the invention can be provided by dissolving the alkali metal salt obtained as above in water, methanol, ethanol, or a mixture thereof and adding one equivalent of calcium chloride or the like.

The solvate (e.g. hydrate, ethanolate) of the compound [I] or salt of the invention also falls within the scope of the invention. The solvate may be obtained, depending on species of compound, by recrystallizing the compound or salt in the corresponding solvent or a suitable mixed solvent containing the corresponding solvent. For example, the hydrate may be obtained by recrystallizing compound [I] from an aqueous alcohol.

The compound [I] of the invention may assume polymorphism. Such polymorphs also fall within the scope of the invention.

The compound [I] of the invention, thus prepared, can be isolated and purified, as a free base or an acid addition salt, by per se known procedures such as concentration, pH adjustment, redistribution, solvent extraction, crystallization, fractional distillation, and chromatography.

The dosage of the compound of the invention as a therapeutic agent for pancreatitis is preferably adjusted in consideration of patient factors such as age and body weight, route of administration, and nature and severity of disease, but the oral dosage for an adult patient, for instance, in terms of the active ingredient of the invention is generally 0.1 mg–50 mg/patient/day and preferably 1 mg–20 mg/patient/day. There may be cases in which higher or lower doses are needed. Moreover, the above daily dosage may be administered in 2–3 divided doses.

The compound of the invention can be administered either as it is or in the form of a pharmaceutical composition containing 0.1%–99.5%, preferably 0.5%–90%, of the compound in a pharmaceutically acceptable nontoxic carrier or vehicle to mammalian animals inclusive of man.

The carrier or vehicle that can be used includes one or more solid, semisolid, or liquid diluents, fillers, or other formulation auxiliaries. The pharmaceutical composition is preferably administered in a unit dosage form. The pharmaceutical composition of the invention can be administered orally, parenterally, locally (e.g. transdermal delivery), or rectally. Of course, the dosage form suited for a selected route of administration should be employed. Oral administration, in particular, is preferred.

Oral administration can be carried out using a solid or liquid unit dosage form such as bulk powders, powders, tablets, dragees, capsules, granules, suspension, solution, syrup, drops or sublingual tablets.

Bulc powders are produced by comminuting the compound of the invention to a suitable particle size. Powders can be manufactured by blending the so-comminuted compound of the invention with a similarly comminuted pharmaceutical carrier such as an edible carbohydrate, e.g. starch, mannitol. Where necessary, a flavorant, preservative, dispersant, color, perfume, etc. may be added.

Capsules can be manufactured by filling capsule shells, e.g. gelatin capsule shells, with the above-mentioned bulc powders or powders or the granules prepared as described hereinafter for tablets. Prior to filling, said powders or granules may be formulated with a lubricant or fluidizing agent such as colloidal silica, talc, magnesium stearate, calcium stearate or solid polyethylene glycol. The availability of the drug after ingestion of capsules can be improved by addition of a disintegrator or solubilizer, such as carboxymethylcellulose, carboxymethylcellulose calcium, low-substitution-degree hydroxypropylcellulose, croscarmellose sodium, carboxymethylstarch sodium, calcium carbonate, sodium carbonate, or the like.

The fine powders of the compound of the invention may be suspended or dispersed in a vegetable oil, polyethylene glycol, glycerin, or a surfactant and wrapped in gelatin sheets to provide soft capsules. Tablets can be manufactured by preparing a powdery mixture containing an excipient, granulating or slugging the mixture, adding a disintegrator or a lubricant, and compressing the whole mixture into the tabular form. The powdery mixture can be prepared by mixing the appropriately comminuted compound with the above-mentioned diluent or base, optionally with addition of a binder (e.g. carboxymethylcellulose sodium, methylcellulose, hydroxypropylmethylcellulose, gelatin, polyvinylpyrrolidone, polyvinyl alcohol), a dissolution retardant (e.g. paraffin), a reabsorption promoter (e.g. quaternary salts), and an adsorbent (e.g. bentonite, kaolin, dicalcium phosphate, etc.). The powdery mixture can be first wetted with a binder such as a syrup, a starch paste, gum arabic, a cellulose solution, or a polymer solution, stirred to mix, dried, and crushed to provide granules. Instead of granulating the powders in this way, it is possible to compress the powders with a tablet machine in the first place and then pulverize the resulting crude-form slugs to provide granules. The granules can be protected from interadhesion by adding a lubricant such as stearic acid, its salt, talc or mineral oil. The lubricated mixture is then compressed. The uncoated tablets thus obtained can be film-coated or sugar-coated.

The compound of the invention can be mixed with a free-flowing inert carrier and directly compressed without resort to the above-mentioned granulation or slugging procedure. Transparent or translucent protective coats such as a hermetic shellac coat as well as sugar or polymer coats and wax glaze coats can also be applied. Other oral compositions, such as a solution, syrup and elixir can also be prepared in unit dosage forms each containing a predetermined amount of the active ingredient. A syrup is prepared by dissolving the compound of the invention in a suitable flavored aqueous medium, and the elixir can be manufactured using a nontoxic alcoholic vehicle. Suspensions can be manufactured by dispersing the compound of the invention in a nontoxic vehicle. Where necessary, a solubilizer or emulsifier (e.g. ethoxylated isostearyl alcohol, polyoxyethylene sorbitol esters), a preservative, a corrigent or flavor (e.g. peppermint oil, saccharin) and others can also be added.

Where necessary, the unit dosage for oral administration can be provided in a microencapsulated form. This kind of preparation may be coated or embedded in a polymer matrix or a wax to insure a prolonged action or sustained release.

For parenteral administration, a liquid unit dosage form for subcutaneous, intramuscular, or intra-venous administration, in the form of a solution or a suspension, can be employed. Such unit dosage forms can be provided by suspending or dissolving a predetermined amount of the compound of the invention in a nontoxic liquid vehicle suitable for injection, such as an aqueous or oily medium, and sterilizing the suspension or solution. For isotonizing such injectable preparations, a nontoxic salt or a solution thereof can be added. In addition, a stabilizer, a preservative, and/or an emulsifier can also be concomitantly used.

Rectal administration can be made by using suppositories manufactured by dissolving or suspending the compound of the invention in a low-melting water-soluble or -insoluble solid base such as polyethylene glycol, cacao butter, semi-synthetic fat (e.g. Witepsol™), higher esters (e.g. myristyl palmitate), or a mixture thereof. The toxicity of the compound of the invention is very low as will be described hereinafter.

The antipancreatitis action of the compound of the invention was confirmed in a test using rats as described hereinafter. The test protocol used is the most popular of all of the test protocols available for the evaluation of therapeutic drugs for pancreatitis in animals. A high correlation has been reported to hold between the antipancreatitis effect found by this test and the clinical effect in man [Yamaguchi et al.: Association of stresses in the onset of pancreatitis, Shoukakika, 18(2), 186–196, 1994).

As test compounds, the following compounds were used.

2-Amino-4-[N,N-bis(2-hydroxyethyl)amino]-6-(2,5-dichlorophenyl)-1,3,5-triazine (compound 1)

(S)-2-Amino-4-(2,5-dichlorophenyl)-6-(2-hydroxymethyl-1-pyrrolidinyl)-1,3,5-triazine hydrochloride (compound 2)

2-Amino-4-(2,5-dichlorophenyl)-6-[(2S,4R)-2-hydroxymethyl-4-hydroxy-1-pyrrolidinyl]-1,3,5-triazine (compound 3)

2-Amino-4-(2,5-dichlorophenyl)-6-morpholino-1,3,5-triazine (compound 4)

Test Example 1

Antipancreatitis activity

Female 12-week-old SD rats were used in groups of 10 individuals. After 40 $\mu$g/kg of cerulein (Cn) was administered intraperitoneally, the animals were placed in stress cages and immersed down to the xiphoid in a constant-temperature bath at 23° C. One hour later, 40 $\mu$g/kg of Cn was administered i.p. again and the stress loading was continued. After 5 hours of stress loading, the animals were sacrificed and laparotomized and the severity of pancreatitis was scored in accordance with the evaluation criteria proposed by Yamaguchi et al. (Gastroenterology 98: 1682–1688, 1990). In addition, the pancreas was excised and its wet weight was determined. As the test compounds, compounds 1, 2, 3, and 4 were administered by oral gavage 18 and 2 hours before the first Cn dosing. As a control compound, irsogladine maleate was used. Statistical significance was tested by Wilcoxon rank sum test for the severity and by Dunnett test for the wet weight. The results are shown in Table 1.

TABLE 1

| Group | Severity of pancreatitis | Wet weight of pancreas (g/kg) |
|---|---|---|
| Untreated control group | 0 | 3.12 ± 0.10 |
| Pancreatitis-induced control group | 2.3 ± 0.33 | 11.12 ± 0.40 |
| Drug-treated group Compound 1 | | |
| 10 mg/kg | 1.4 ± 0.22* | 9.33 ± 0.66 |
| 30 mg/kg | 0.6 ± 0.22** | 7.13 ± 0.57** |
| 100 mg/kg | 0.3 ± 0.21** | 5.65 ± 0.40** |
| Pancreatitis-induced control group Drug-treated group | 2.4 ± 0.27 | 7.92 ± 0.51 |

TABLE 1-continued

| Group | Severity of pancreatitis | Wet weight of pancreas (g/kg) |
|---|---|---|
| Compound 2 | | |
| 1 mg/kg | 1.3 ± 0.30* | 6.86 ± 0.41 |
| 3 mg/kg | 0.8 ± 0.29** | 6.83 ± 0.48 |
| 10 mg/kg | 0.4 ± 0.16** | 7.31 ± 0.64 |
| 30 mg/kg | 0.1 ± 0.03** | 4.35 ± 0.32** |
| Pancreatitis-induced control group | 2.5 ± 0.05 | 8.12 ± 0.46 |
| Drug-treated group Compound 3 | | |
| 3 mg/kg | 1.4 ± 0.10* | 7.58 ± 0.36 |
| 10 mg/kg | 0.7 ± 0.08** | 6.67 ± 0.37 |
| 30 mg/kg | 0.6 ± 0.08** | 5.96 ± 0.70** |
| Pancreatitis-induced control group | 1.9 ± 0.18 | 8.22 ± 0.35 |
| Drug-treated group Compound 4 | | |
| 10 mg/kg | 0.9 ± 0.28* | 7.33 ± 0.23 |
| 30 mg/kg | 0.5 ± 0.22* | 6.18 ± 0.53* |
| 100 mg/kg | 0.5 ± 0.17** | 7.49 ± 0.47 |
| Pancreatitis-induced control group | 2.3 ± 0.33 | 11.12 ± 0.40 |
| Control compound-treated group | | |
| 10 mg/kg | 2.2 ± 0.33 | 10.09 ± 0.51 |
| 30 mg/kg | 1.5 ± 0.27 | 8.52 ± 0.60** |
| 100 mg/kg | 0.4 ± 0.22** | 7.14 ± 0.58** |

Each value represents mean ± S.E.
*: P < 0.05
**: P < 0.01 severity of pancreatitis in a dose-dependent fashion over the range of 1–100 mg/kg and inhibited the gain in wet weight of pancreas at 30 mg/kg and higher doses. On the other hand, the control compound irsogladine maleate was almost equivalent to the compound of the invention in the effect on wet weight of pancreas but showed a significant reducing effect on the severity of pancreatitis only at 100 mg/kg, thus being considerably less effective than the compound of the invention.

The above results indicate that the compound of the invention is as inhibitory as the control compound against swelling of the pancreas and about 3 to 100-fold as potent as the control compound in antipancreatitis action. Incidentally, the mechanisms of this antipancreatitis action remain to be elucidated as yet.

Test Example 2

Effect on body weight gain

Compound 1 was administered orally to 6-week-old male SD rats (in groups of 5) daily to investigate its effect on body weight gain. Even when 1000 mg/kg was administered daily for 2 consecutive weeks, compound 1 did not affect the body weight gain of rats.

Test Example 3

Acute toxicity

Six-week-old male mice (BALB/c) fasted in advance was orally dosed with 1 g/kg or 500 mg/kg of the test compound and the time course of mortality was monitored for 1 week. The test compound was suspended in 0.5% aqueous methylcellulose solution and administered in the dose of 500 or 1,000 mg/20 ml/kg. As a result, no death was encountered at the dose level of 1 g/kg for compounds 1, 3, and 4 and at the dose level of 500 mg/kg for compound 2. The toxicity of the compound of the invention is, thus, extremely low.

BEST MODE OF CARRYING OUT THE INVENTION

The following production and working (formulation) examples are intended to describe the present invention in further detail and should by no means be interpreted as defining the scope of the invention.

Production Example 1

2-Amino-4-[N,N-bis(2-hydroxyethyl)amino]-6-(2,5-dichlorophenyl)-1,3,5-triazine (compound 1)

To a mixture of 9.2 g of diethanolamine, 200 ml of N,N-dimethylformamide, and 15 g of anhydrous potassium carbonate was added 20 g of 2-amino-4-chloro-6-(2,5-dichlorophenyl)-1,3,5-triazine with stirring at room temperature and the mixture was further stirred at room temperature for 7 hours. This reaction mixture was diluted with 2L (liters) of water with stirring and then stirred for 1 hour. The resulting crystal crop was harvested by filtration, rinsed with water, and dried to obtain 24 g of white crystals. Those crystals were recrystallized from methanol, collected by filtration, and dried to provide 21 g of the title compound as white crystals. m.p. 199°–200° C.

Elemental analysis ($C_{13}H_{15}Cl_2N_5O_2$)
  Calcd. (%): C, 45.36; H, 4.39; N, 20.35
  Found (%): C, 45.58; H, 4.33; N, 20.46

Production Example 2

(S)-2-amino-4-(2,5-dichlorophenyl)-6-(2-hydroxymethyl-1-pyrrolidinyl)-1,3,5-triazine hydrochloride (compound 2)

In 50 ml of methanol was dissolved 5.1 g of the compound obtained using (S)-2-hydroxymethylpyrrolidine in lieu of diethanolamine in otherwise the same manner as Example 1 and 6 ml of 20% HCl/methanol was added under cooling. The solvent was then concentrated to about 1/10 of the initial volume and the resulting crystal crop was harvested by filtration to provide 2.6 g of the title compound as white crystals. m.p. 143°–145° C.

Elemental analysis ($C_{14}H_{15}Cl_2N_5O \cdot HCl \cdot H_2O$)
  Calcd. (%): C, 42.60; H, 4.60; N, 17.74
  Found (%): C, 42.34; H, 4.61; N, 17.79

Production Example 3

2-Amino-4-(2,5-dichlorophenyl)-6-[(2S,4R)-2-hydroxymethyl-4-hydroxy-1-pyrrolidinyl]-1,3,5-triazine (compound 3)

Except that (2S,4R)-4-hydroxy-2-hydroxymethyl-pyrrolidine was used in lieu of diethanolamine, the procedure of Example 1 was otherwise repeated to provide the title compound as white powders.

Elemental analysis ($Cl_4H_{15}Cl_2N_5O_2 \cdot \frac{1}{2}EtOH \cdot \frac{1}{2}H_2O$)
  Calcd. (%): C, 46.40; H, 4.93; N, 18.04
  Found (%): C, 46.36; H, 4.80; N, 18.24 H-NMR (CDCl$_3$)
  δ: 1.7–2.0 (1H, m), 2.1–2.25 (1H, m),
  2.67 (1H, bs), 3.4–3.85 (3H, m), 3.95–4.25 (1H, m),
  4.35–4.55 (2H, m), 5.53 (2H, d, J=11 Hz), 7.25–7.4 (2H, m),
  7.65 (1H, d, J=19 Hz).

Production Example 4

2-Amino-4-(2,5-dichlorophenyl)-6-morpholino-1,3,5-triazine (compound 4)

Except that morpholine was used in lieu of diethanolamine, the procedure of Production Example 1 was otherwise repeated to provide the title compound. m.p. 189°–191° C.

Elemental analysis ($C_{13}H_{13}Cl_2N_5O$)
 Calcd. (%): C, 47.87; H, 4.02; N, 21.47
 Found (%): C, 47.85; H, 3.92; N, 21.52

Production Example 5

2-Amino-4-(2,5-dichlorophenyl)-6-[(2S,4R)-2-hydroxymethyl-4-hydroxy-1-pyrrolidinyl]-1,3,5-triazine (compound 3)

Step 1

Using trans-4-hydroxy-L-proline methyl ester in lieu of diethanolamine, the procedure of Production Example 1 was otherwise repeated to provide 2-amino-4-(2,5-dichlorophenyl)-6-[(2S,4R)-2-methoxycarbonyl-4-hydroxy-1-pyrrolidinyl]-1,3,5-triazine as white powders.

Step 2

To a mixture of 20.9 g of lithium aluminum hydride and 1000 ml of tetrahydrofuran under ice-cooling and stirring, a solution of 100 g of the compound obtained in Step 1 in 300 ml of tetrahydrofuran was added gradually dropwise at 0°–5° C. and the reaction was carried out at the same temperature for 3 hours. After the excess lithium aluminum hydride was decomposed, the reaction mixture was filtered and the filtrate was concentrated. The residue was dissolved in ethyl acetate and the solution was washed with water, dried, and concentrated to give a white solid. This solid was recrystallized from ethyl acetate, collected by filtration, and dried to provide 74.7 g of the title compound as white crystals. m.p. 171°–173° C.

Elemental analysis ($C_{14}H_{15}Cl_2N_5O_2$)
 Calcd. (%): C, 47.21; H, 4.24; N, 19.66
 Found (%): C, 47.19; H, 4.32; N, 19.55 $[\alpha]^{20}_D$=−67.80° (MeOH, c=1.053)

Formulation Example 1

Two (2) grams of compound 1 is weighed and mixed evenly with 70 g of lactose and 30 g of corn starch, followed by addition of 25 ml of 16% hydroxypropylcellulose solution. This mixture is agitation-granulated. After drying, the granules are size-selected, mixed with 2 g of magnesium stearate and 2 g of talc, and compressed with a rotary tablet machine to provide tablets.

Recipe

In 110 mg per tablet,

| | |
|---|---|
| Compound 1 | 2 mg |
| Lactose | 70 mg |
| Corn starch | 30 mg |
| Hydroxypropylcellulose | 4 mg |
| Magnesium stearate | 2 mg |
| Talc | 2 mg |

Formulation Example 2

Four (4) milligrams of compound 1 is weighed and mixed evenly with 996 mg of lactose to provide pharmaceutical powders.

INDUSTRIAL APPLICABILITY

Since the compound of the invention is a safe compound having potent antipancreatitis activity with a low toxic potential as described above, it is useful for the treatment and prevention of pancreatitis in mammals inclusive of man.

What is claimed is:

1. A method for the therapy of pancreatitis which comprises administering an effective amount of a compound of formula [I] or a salt thereof or a solvate thereof, to a human being or an animal in need thereof:

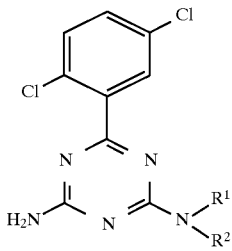

wherein $R^1$ is hydrogen, alkyl optionally substituted, aralkyl, arylalkenyl, or aryl and $R^2$ is alkyl optionally substituted, aralkyl, arylalkenyl, or aryl; or $R^1$ and $R^2$ when taken together with the adjacent N atom, as $NR^1R^2$, is a 4 through 8-membered cyclic amino group, which cyclic amino group optionally contains nitrogen, oxygen, or sulfur as a ring member, in addition to said N atom, with said cyclic amino group being optionally substituted.

2. The method for the therapy of pancreatitis as claimed in claim 1, wherein $R^1$ is (1) hydrogen; (2) alkyl optionally substituted by hydroxy, alkoxy, amino, monoalkylamino, dialkylamino, arylamino, 4 through 8-membered cyclic amino, carboxy, cabamoyl, aryloxy, and acyloxy; (3) aralkyl; (4) arylalkenyl; or (5) aryl; and $R^2$ is (1) alkyl optionally substituted by hydroxy, alkoxy, amino, monoalkylamino, dialkylamino, arylamino, 4 through 8-membered cyclic amino, carboxy, carbamoyl, aryloxy, and acyloxy; (2) aralkyl; (3) arylalkenyl; or (4) aryl.

3. The method for the therapy of pancreatitis as claimed in claim 1, wherein $NR^1R^2$ of the compound is 4 through 8-membered optionally substituted by hydroxy, oxo, carboxy, alkyl, hydroxyalkyl, aryloxyalkyl, aminoalkyl, alkylsulfonylaminoalkyl, alkylsulfonylamino, alkylsulfonylaralkyl, alkylsulfonyl, aryl, aralkyl, and 2-pyrimidinyl.

4. The method for the therapy of pancreatitis as claimed in claim 1, wherein $R^1$ and $R^2$ are the same or different and each is hydroxyalkyl or $NR^1R^2$ is pyrrolidin-1-yl, piperidino, or morpholino, optionally substituted.

5. The method for the therapy of pancreatitis as claimed in claim 1, wherein $NR^1R^2$ is pyrrolidin-1-yl, piperidino, or morpholino, optionally substituted by hydroxy, hydroxyalkyl, oxo, alkyl, amino, or aminoalkyl.

6. The method for the therapy of pancreatitis as claimed in claim 1, wherein the compound is selected from the group consisting of 2-amino-4 -[N,N-bis(2-hydroxyethyl)amino]-6-(2,5-dichlorophenyl)-1,3,5-triazine; (S)-2-amino-4-(2,5-dichlorophenyl)-6-(2-hydroxymethyl-1-pyrrolidinyl)-1,3,5-triazine hydrochloride; 2-amino-4-(2,5-dicholorophenyl)-6-[(2S,4R)-2-hydroxymethyl-4-hydroxy-1-pyrrolidinyl]-1,3,5-triazine; and 2-amino-4-(2,5-dichlorophenyl)-6-morpholino-1,3,5-triazine.

7. 2-amino-4-(2,5-dicholorophenyl)-6-[(2S,4R)-2-hydroxymethyl-4-hydroxy-1-pyrrolidinyl]-1,3,5-triazine, or a salt thereof, or a hydrate thereof or a salt thereof.

8. A pharmaceutical composition for the therapy of pancreatitis which comprises an effective amount of 2-amino-4-(2,5-dicholorophenyl)-6-[(2S,4R)-2-hydroxymethyl-4-hydroxy-1-pyrrolidinyl]-1,3,5-triazine, or a salt thereof, or a hydrate thereof or a salt thereof.

9. A method for the therapy of pancreatitis which comprises administering to a human being or an animal in need thereof an effective amount of 2-amino-4-(2,5-dicholorophenyl)-6-[(2S,4R)-2-hydroxymethyl-4-hydroxy-1-pyrrolidinyl]-1,3,5-triazine, or a salt thereof, or a hydrate thereof or a salt thereof.

* * * * *